US012797250B2

(12) United States Patent
Batte

(10) Patent No.: US 12,797,250 B2
(45) Date of Patent: Nov. 17, 2026

(54) MONITORING BANDAGE APPARATUS AND METHOD OF USE THEREOF

(71) Applicant: Edwin Batte, Hoover, AL (US)

(72) Inventor: Edwin Batte, Hoover, AL (US)

( * ) Notice: Subject to any disclaimer, the term of this patent is extended or adjusted under 35 U.S.C. 154(b) by 704 days.

(21) Appl. No.: 18/207,911

(22) Filed: Jun. 9, 2023

(65) Prior Publication Data

US 2024/0407953 A1 Dec. 12, 2024

(51) Int. Cl.
*A61F 13/00* (2024.01)
*A61F 13/02* (2024.01)

(52) U.S. Cl.
CPC .... *A61F 13/00059* (2013.01); *A61F 13/0266* (2013.01); *A61F 2013/00412* (2013.01); *A61F 2013/00948* (2013.01); *A61F 2013/00953* (2013.01)

(58) Field of Classification Search
CPC .... A61J 1/2027; A61M 5/282; A61M 5/2425; A61M 15/0031; A61F 13/00059; A61F 13/0266; A61F 2013/00412; A61F 2013/00948; A61F 2013/00953
USPC .......................................... 604/87; 602/41–42
See application file for complete search history.

(56) References Cited

U.S. PATENT DOCUMENTS

| | | | | |
|---|---|---|---|---|
| 4,408,557 A * | 10/1983 | Bradley | G01K 3/04 368/327 |
| 4,947,867 A * | 8/1990 | Keeton | A61F 13/00059 40/586 |
| 2004/0118710 A1* | 6/2004 | Bourque | B65D 75/563 206/219 |
| 2020/0054279 A1* | 2/2020 | Krupnick | A61B 5/0002 |

FOREIGN PATENT DOCUMENTS

| | | | | |
|---|---|---|---|---|
| EP | 1645856 A1 * | 4/2006 | G01K 3/04 |
| EP | 3669147 B1 * | 9/2023 | G01P 15/04 |
| WO | WO-2018005669 A1 * | 1/2018 | A61F 13/0243 |
| WO | WO-2018115461 A1 * | 6/2018 | A61F 13/00085 |

* cited by examiner

*Primary Examiner* — Caitlin A Carreiro
(74) *Attorney, Agent, or Firm* — Kevin H. Hazen; Hazen Patent Group, LLC

(57) ABSTRACT

A method is described for monitoring a wound site of a patient, including the steps of: (1) applying a force to a breakable barrier of a bandage to activate a time sensor at an initial time of application of the bandage; (2) monitoring elapsed time since application of the bandage through total migration length of a fluid from a reservoir into a migration zone; and (3) demarking time through progression of a colored fluid from the reservoir into the migration zone with calibrated time points printed on the bandage, such as in a PICC line assembly.

11 Claims, 15 Drawing Sheets

MONITORING BANDAGE APPARATUS AND METHOD OF USE THEREOF

BACKGROUND OF THE INVENTION

Field of the Invention

The invention relates to a monitoring bandage, such as for treating wounds.

Discussion of the Prior Art

Problem

Infections at wound sites continue to be a persistent problem worldwide.

Central lines are used to: draw blood, administer medications, and/or introduce fluids/medicines to a patient, such as a critically ill person. Central lines are in common use throughout the United States in the acute, post-acute, and home health care industry. Central line-associated bloodstream infection (CLABSI) is a primary laboratory confirmed bloodstream infection in patients with a central line at the time of onset of symptoms, where the infection is not related to an infection from another site. Central lines cause approximately 2,000,000 infections annually, result in 80,000 lives lost, and cost over $45 billion in unnecessary healthcare costs. Further, a patient discharged with a central line or peripherally placed central line (PICC) is twenty-five percent more likely to readmit, where a PICC line is usually applied to the upper arm.

What is needed is a device/system/apparatus for reducing the number of infections at central line/PICC administration sites on patients.

SUMMARY OF THE INVENTION

The invention comprises a bandage configured with an indicator, such as a colorimetric indicator, to indicate elapsed time since application of the bandage, such as on a wound site and/or a central line/PICC line application site.

DESCRIPTION OF THE FIGURES

A more complete understanding of the present invention is derived by referring to the detailed description and claims when considered in connection with the Figures, wherein like reference numbers refer to similar items throughout the Figures.

Elements and steps in the figures are illustrated for simplicity and clarity and have not necessarily been rendered according to any particular sequence. For example, steps that are performed concurrently or in different order are illustrated in the figures to help improve understanding of embodiments of the present invention.

DETAILED DESCRIPTION OF THE INVENTION

The invention comprises a method for monitoring a wound site of a patient, comprising the steps of: (1) applying a force to a breakable barrier of a bandage, applied to the wound site, to activate a time sensor at an initial time of application of the bandage; (2) monitoring elapsed time since application of the bandage through total migration length of a fluid from a reservoir into a migration zone, and (3) demarking time through progression of a colored fluid from the reservoir into the migration zone with calibrated time points printed on the bandage, such as in a PICC line assembly. Optionally and preferably, the breakable barrier is breached through a force of any of: applying a downward signing force across a frangible seam, peeling an adhesive backing off of the bandage, stretching an adhesive tape used to secure the PICC line, and rotating a valve.

In one embodiment, a time based visualization device, implemented at a central line/PICC site, is used to indicate one or more of: (1) elapsed time since bandage application and (2) a time to change the bandage/dressing. The visual indicator is visible to: a care giver, such as a catheter giver; the patient; and/or anyone in sight of the bandage, such as an administrator, inspector, and/or family, as further described infra.

Herein, a bandage refers to medical dressing, gauze, and/or an adhesive bandage. Bandages function to protect a wound/scab from friction, bacteria, damage, and dirt, which aids the healing process Herein, an adhesive bandage is a small, flexible sheet of material which is sticky on one side, with a smaller, non-sticky, absorbent pad stuck to the sticky side. The pad is placed against the wound, and overlapping edges of the sticky material are pressed into contact with surrounding skin. A backing covering the adhesive side is optionally and preferably just prior to application of the bandage to a wound.

Herein, an adhesive sheet is optionally a woven fabric, a plastic, such as PVD, polyethylene, and/or a polyurethane, and/or a latex strip, that is optionally waterproof. The adhesive is optionally an acrylate and/or a vinyl resin.

Herein, an absorbent pad is a thin, porous padding that is optionally coated with a porous-polymer coating to keep it from sticking to the wound. The pad is optionally medicated, such as with an antibiotic and/or an antiseptic.

Herein, an x-axis is a relative axis extending along a length of a body part, such as an arm, leg, or neck; a y-axis extends across the body part; and a z-axis extends perpendicularly from an x/y-plane formed from the x-axis and the y-axis.

Figure 1:
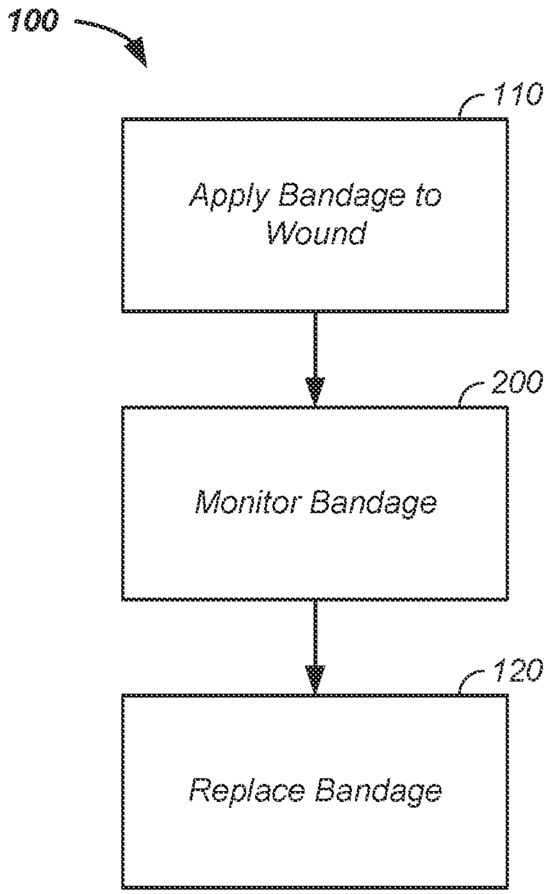
FIG. 1 illustrates a process of applying, monitoring, and removing a bandage.

Referring now to FIG. 1, a bandage monitoring system 100 is illustrated. In a first process, a bandage is applied to a wound 110. For example, a bandage is applied to a cut, scrape, suture, stitches, central line site, and/or a PICC site. For clarity of presentation and without loss of generality, examples of bandages/dressings at a PICC site are provided, where the examples optionally and preferably apply to any wound site on a person or a non-person animal, such as a pet. In a second process, the bandage is monitored in a bandage monitoring step 200, which is further described infra. Generally, the monitoring process is optionally and preferably aided with one or more colorimetric indicators, again as further described infra. In a third process, the bandage is replaced 120, such as based, at least in part, on the colorimetric indicator.

Figure 2:
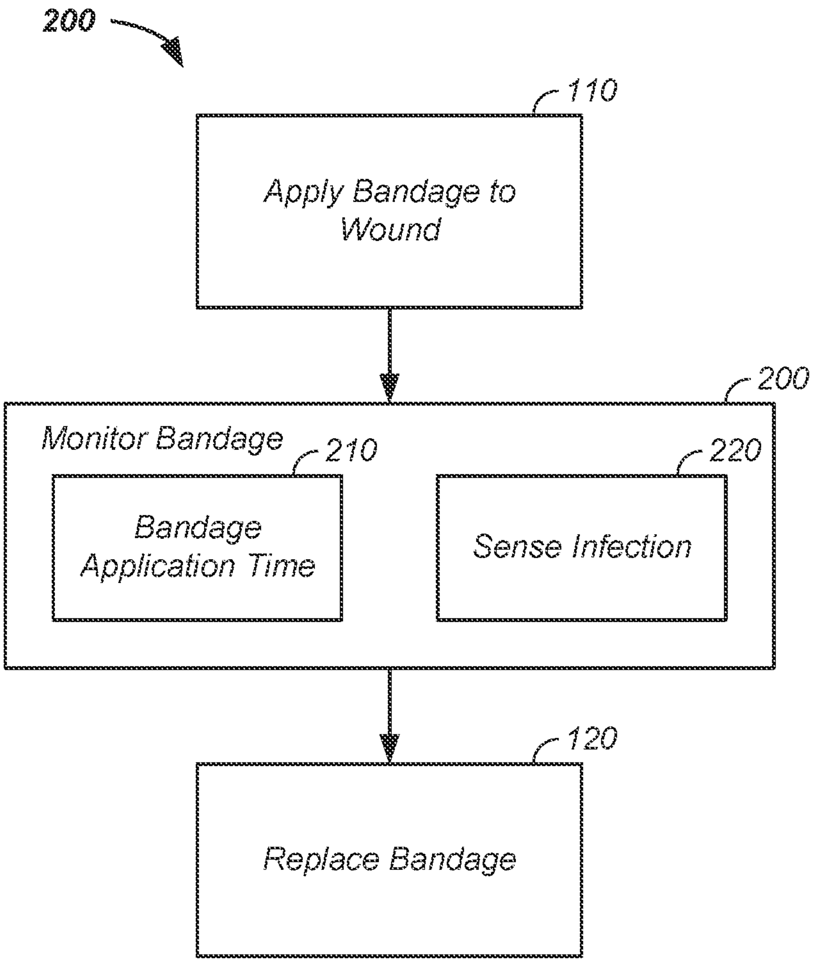
FIG. 2 illustrates monitoring a bandage.

Referring now to FIG. 2, the bandage monitoring system 100 is further described. As illustrated, the bandage monitoring step 200 optionally indicates: a bandage application elapsed time 210, such as a total time since the bandage was applied to a wound, and/or an infection sensing step 220, both of which are further described infra.

Figure 3:
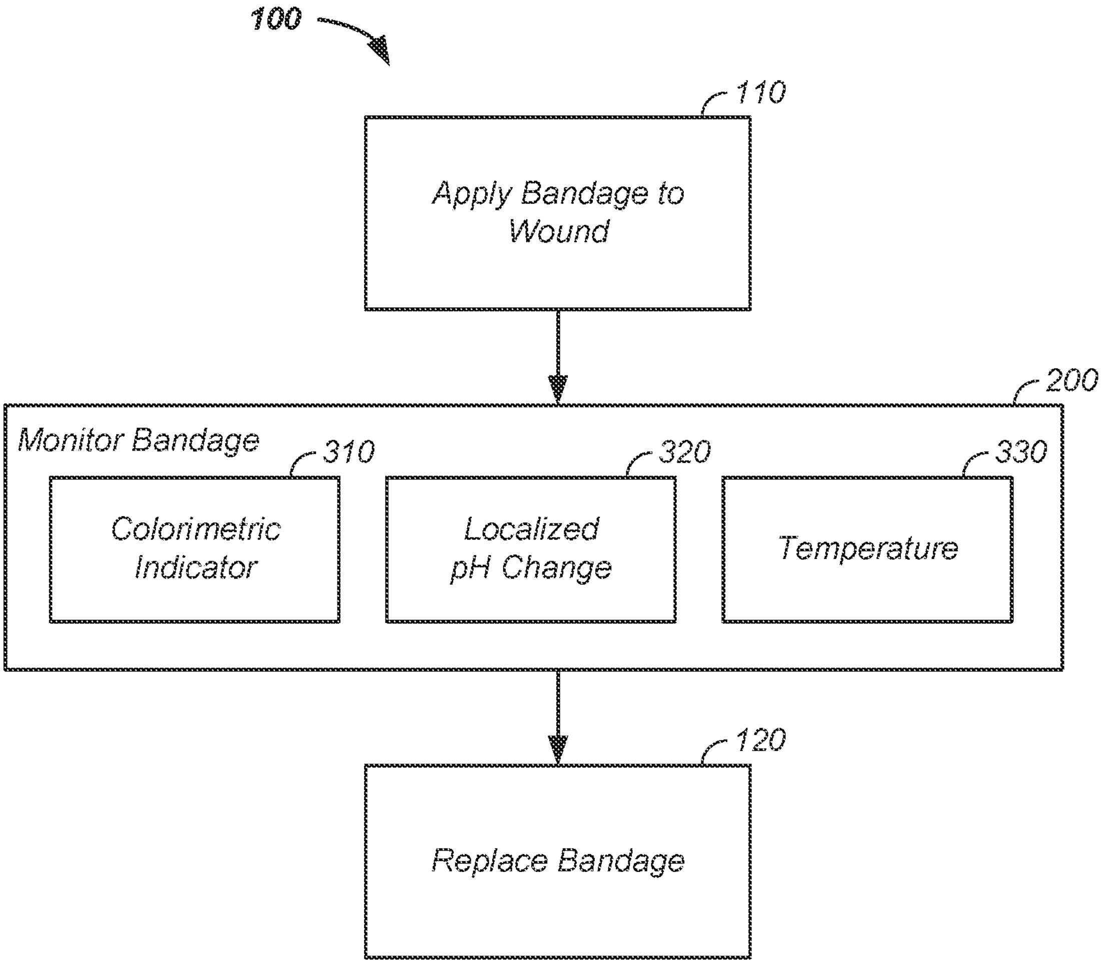
FIG. 3 illustrates sensing state of a bandage.

Referring now to FIG. 3, the bandage monitoring system 100 is further described. As illustrated, the bandage monitoring step 200 optionally uses any one or more of: a colorimetric indicator 310, such as one or more colors indicating elapsed time(s); a localized pH change, such as an acidic deviation indicating a localized infection; and/or a temperature change, such as a local temperature increase indicating a localized infection.

Figure 4A:
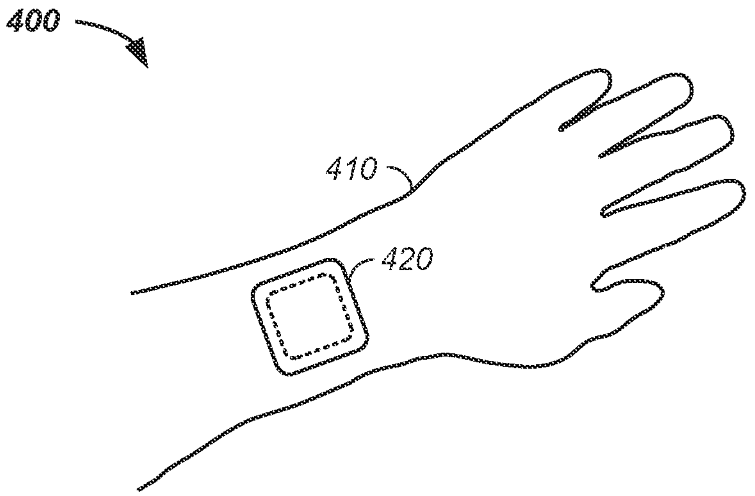
FIG. 4A illustrates a bandage on a wound and FIG. 4B illustrates time, infection, and temperature sensors.
Figure 4B:
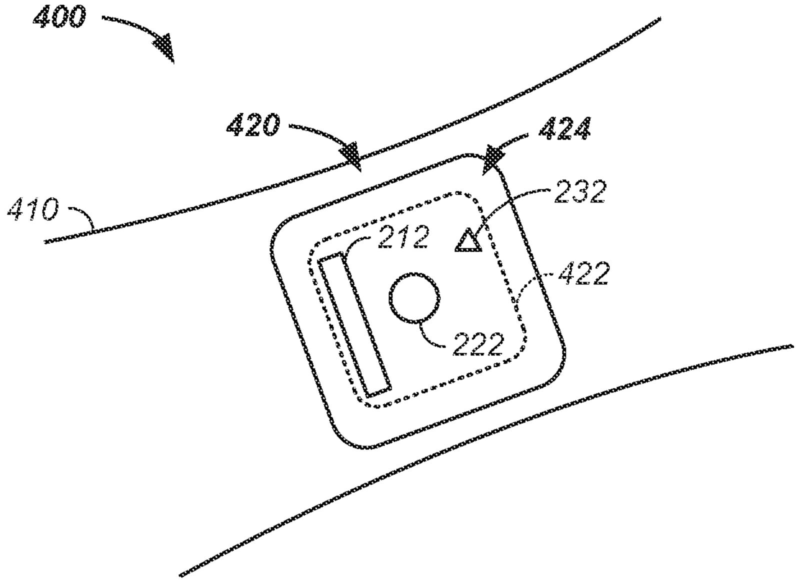

Referring now to FIG. 4A, a bandage sensor application 400 is illustrated, such as applying to a wound site of a person/patient 410 a bandage 420. Referring still to FIG. 4A and referring now to FIG. 4B, the bandage 420 is illustrated with an optional and preferred adhesive layer 424, such as with an adhesive side on the body side, affixing an underlying bandage pad 422 to the patient 410. Optionally, the adhesive layer 424 covers all or at least 20, 40, 60, 70, 80, or 90 percent of the bandage pad 422 and preferably the bandage pad 422 extends beyond the bandage pad 422 in at least two directions from the bandage pad, such as on opposite sides of the wound along the x-axis and/or the y-axis. Still referring to FIG. 4B, the bandage 420 is illustrated with one or more of an optional: time sensor 212, pH sensor 222, and/or temperature sensor 232.

Example I

Figure 5:
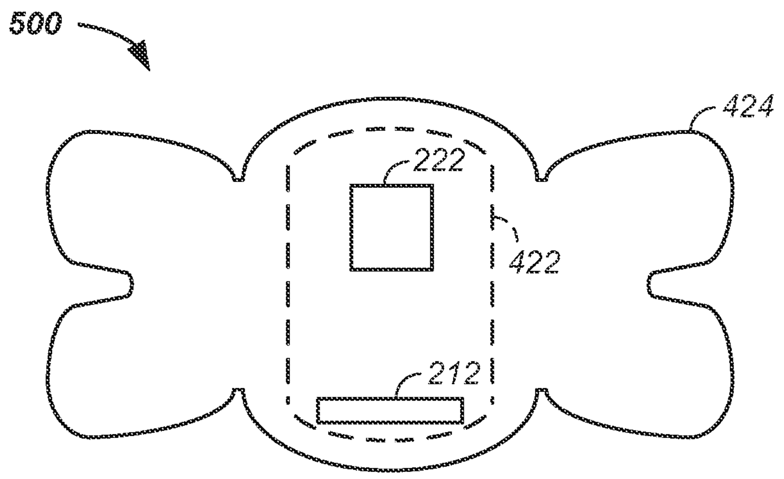
FIG. 5 illustrates an intelligent butterfly bandage.

Referring now to FIG. 5, a flexible 4-wing bandage or flexible butterfly bandage 500 is illustrated with a single-sided adhesive layer 424 affixing a bandage pad 422, such as a gauze layer, to the patient, where the flexible butterfly bandage 500 is configured with one or more of: a time sensor 212 and a pH sensor 222.

Example II

Figure 6:
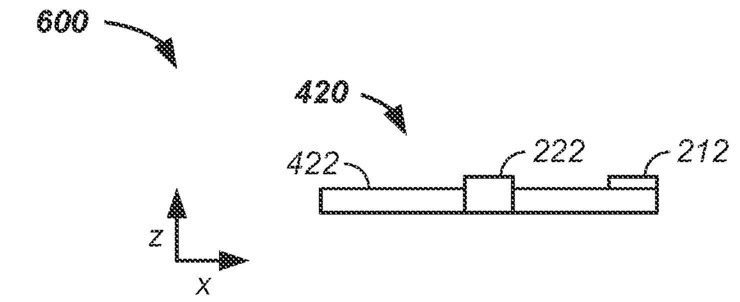
FIG. 6 illustrates intelligent gauze.

Referring now to FIG. 6, an example of an intelligent gauze 600 is illustrated, where the bandage 420 includes a bandage pad 422, such as gauze, with a time sensor 212 and/or a pH sensor 222 attached to the bandage pad 422.

Example III

Figure 7:
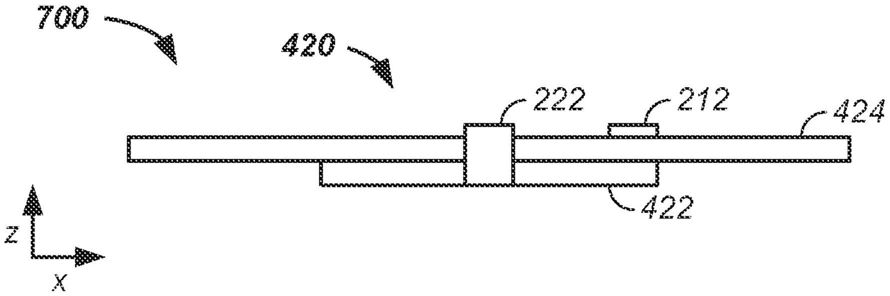
FIG. 7 illustrates an intelligent bandage.

Referring now to FIG. 7, an example of an intelligent bandage 700 is illustrated, where the bandage 420 includes a time sensor 212 attached to an adhesive layer 424 and/or an adhesive strip, such as a strip configured with adhesive on one side, and/or a pH sensor 222 penetrating through at least one of the bandage pad 422 and the adhesive layer 424, such as into contact with the wound. Contact of the pH sensor with the wound optionally allows analysis of pH of the aqueous based seepage from the wound with a pH sensing device, such as a chemical/electrochemical pH sensor.

Example IV

Figure 8:
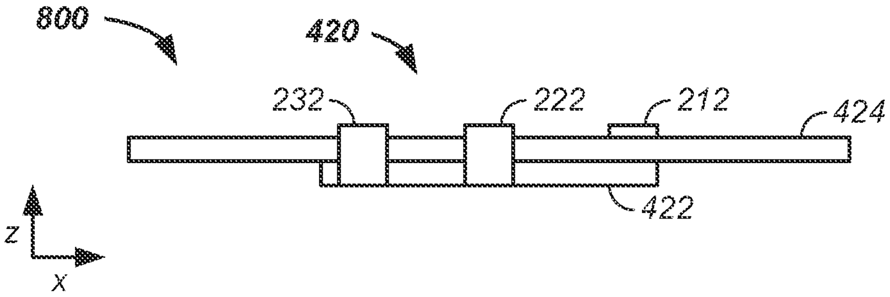
FIG. 8 illustrates a smart wound cover.

Referring now to FIG. 8, an example of an intelligent wound cover 800 is illustrated, where the bandage 420 includes a time sensor 212 attached to an adhesive layer 424 and/or an adhesive strip, such as a strip configured with adhesive on one side; a pH sensor 222 penetrating through at least one of the bandage pad 422 and the adhesive layer 424, such as into contact with the wound; and/or a temperature sensor 232, such as a temperature sensor 232 optionally in physical contact with the patient (not illustrated). For instance, the temperature sensor 232 optionally penetrates through the bandage pad 422 and/or the adhesive layer 424, which allows reading the temperature sensor without removal of the bandage from the patient and allows the temperature sensor to contact skin of the patient.

PICC Line

Figure 9:
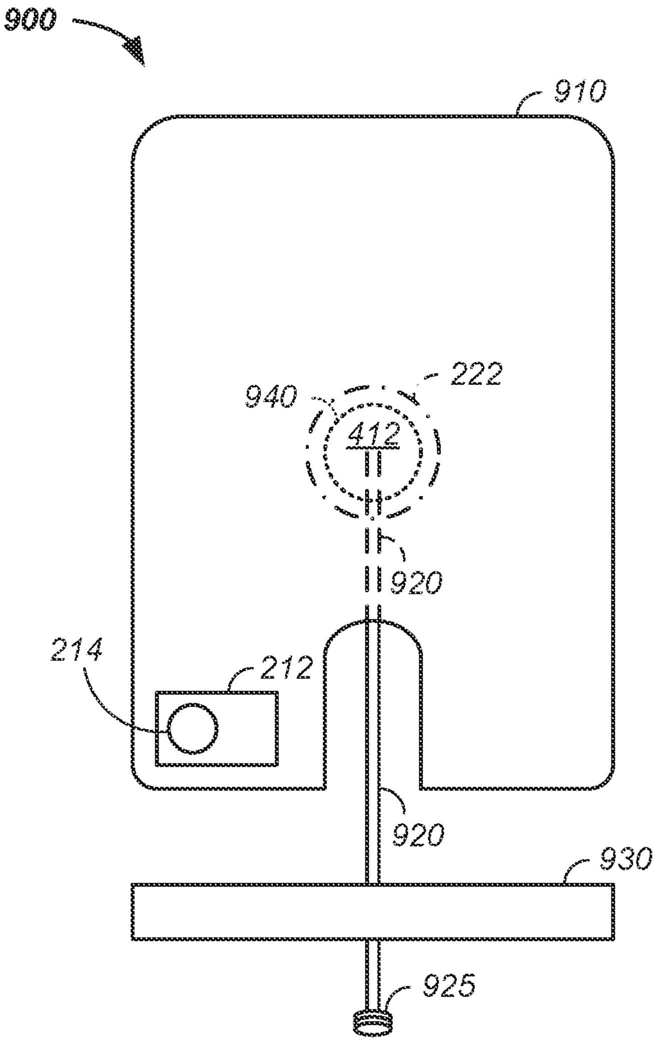
FIG. 9 illustrates a PICC line assembly.

Referring now to FIG. 9, a PICC line 900/PICC line assembly is illustrated. In this example of the PICC line 900, a single sided adhesive patch 910, which is an example of an adhesive layer 424, holds a catheter 920, inserted into a vein of the patient during use, in place. Optionally and preferably, the adhesive layer is transparent, such as to allow visualization of the pH sensor 222 and/or the time sensor 212. Optionally and preferably, the catheter 920 includes a luer connector 925, such as for attachment to an IV bag. An adhesive tape 930 is optionally and preferably used to help secure the catheter 920 in place. An optional pH sensor 222 is located proximate, on, and/or within 1, 2, 3, 4, 5, 10, or 15 mm of an insertion location 412 of the catheter 920 into the patient. An optional antimicrobial patch 940 is optionally included as part of the PICC line assembly, such as circumferentially positioned around the insertion location 412. A time sensor 212 with an activation button 214 is optionally and preferably included with the PICC line kit. The time sensor 212 is optionally included as an element of the adhesive tape 930, as further described infra.

Time Sensor

Figure 10:
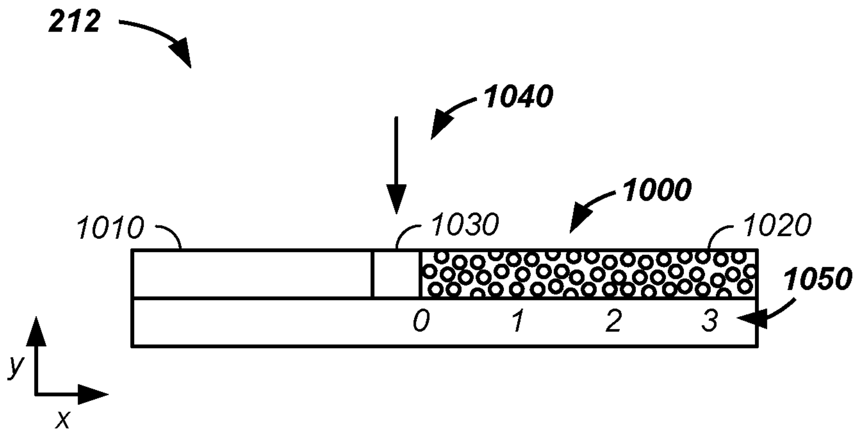
FIG. 10 illustrates a time sensor/time sensor on a strip.

Referring now to FIG. 10, an example of the time sensor 212 is illustrated. As illustrated, the time sensor 212 includes a strip 1000 of any geometry, where the geometry allows space for a migration of a mobile phase contained in a reservoir 1010 into a migration zone 1020. The time sensor 212 is optionally integrated into any part of the bandage 420; PICC line 900/PICC line assembly; and/or adhesive tape 930. Still referring to FIG. 10, generally, a barrier 1030, such as a frangible seam or port separates the mobile phase in the reservoir 1010 from the migration zone 1020. In this example, a force 1040 forms an opening in a frangible seam, an example of the barrier 1030, at an initial time, to. At the start of the initial time, the mobile phase starts to diffuse into the migration zone 1020. Progress of the mobile phase is demarked by calibrated time points 1050, such as with printed time points. For instance, if the mobile phase is red, the red mobile phase reaches time indicators 1, 2, and 3 at three distinct times, such as denoted in minutes or hours. In one case, the time indicators 1, 2, and 3 indicate 1, 2, and 3 days respectively. The elapsed time is optionally any time period from 10 minutes to 60 days. The application force and barrier are further described infra. The mobile phase is optionally and preferably any liquid, such as a liquid of any color. The liquid is optionally an indicator that changes color with time. However, optionally and preferably the liquid is simple colored and indicates passage of time by the distance traveled in the migration zone 1020. The migration zone is optionally and preferably a solid phase that slows diffusion of the liquid phase.

Figure 11:
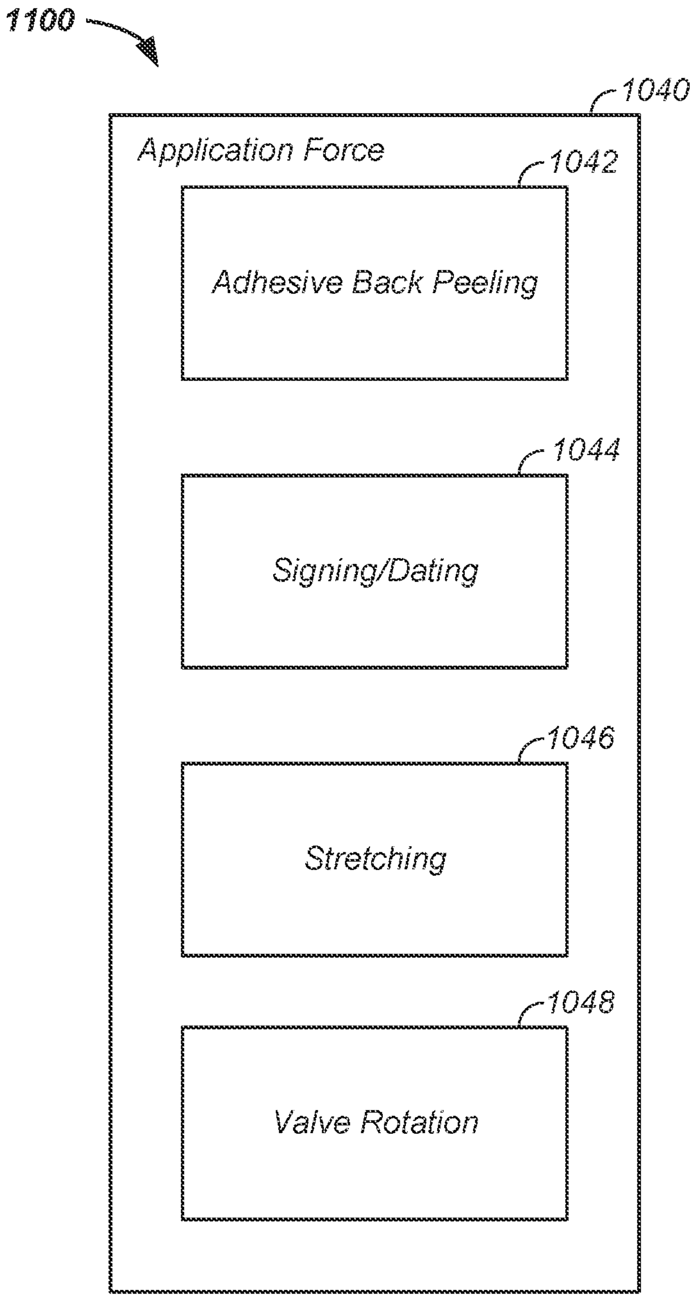
FIG. 11 illustrates application forces triggering a start of the time sensor use.

Referring now to FIG. 11, force application methods 1100 are further described. Generally, the force 1040 is any force and/or movement of a mechanism that initiates movement of the mobile phase from the reservoir 1010 into the migration zone 1020. Examples of application forces 1040 are provided herein. In a first example, the force 1040 of peeling off an adhesive backing 1042 is sufficient to rupture a frangible seam, which is an example of the barrier. In a second example, the force 1040 of a pen or marking device in an action of signing/dating 1044 is sufficient to rupture a frangible seam. In a third example, the force 1040 of breaking the barrier 1030 or forming a rupture in the barrier 1030 is a force of stretching 1046, such as stretching the adhesive tape 930, such as with a time sensor 212 embedded and/or attached to the adhesive tape 930 used to secure the catheter 920. In a fourth example, the force 1040 used to initiate flow of the mobile phase from the reservoir 1010 into the migration zone 1020 is a force applied to open a valve or rotate a valve 1048. Examples of applying the force through peel of backing, signature pressing, and valve rotation are provided infra.

Example I

Figure 12:
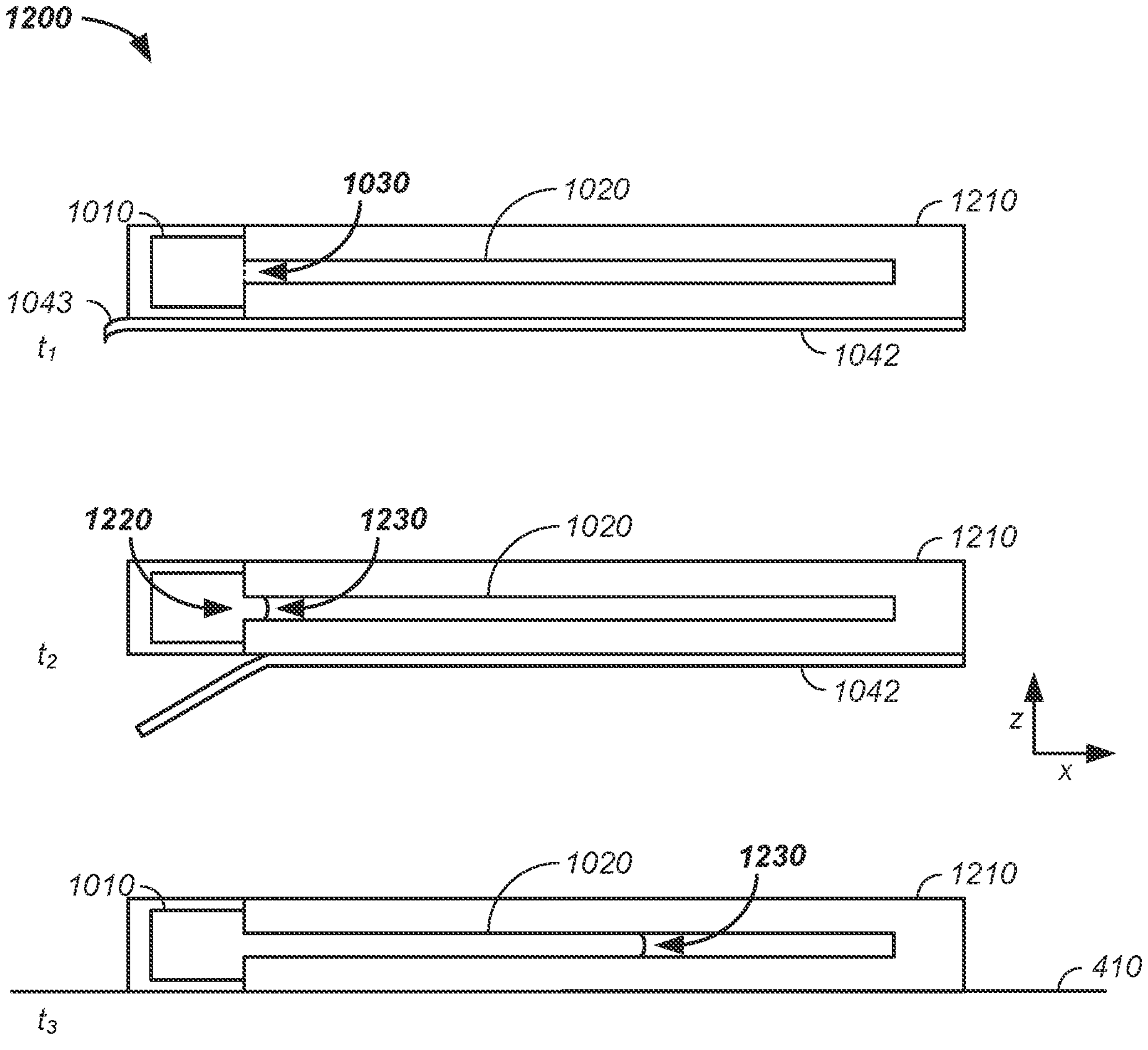
FIG. 12 illustrates an adhesive backed time sensor.

Referring now to FIG. 12, an example of an adhesive backed time sensor 1200 is illustrated, which is optionally and preferably an element of the bandage 420 and/or PICC line assembly 900. In this example of a time sensor strip 1210, the time sensor 212 has a reservoir 1010 and a migration zone 1020 on a strip, where the barrier 1030 is a frangible barrier that is ruptured by the force of removal of the adhesive back 1042. The adhesive back 1042 has an optional tab 1043 that is grasped, such as by a caregiver, at a first time, t1. At a second time, t2, as the adhesive 1042 is pulled back from the time sensor strip 1210, lateral forces disrupt the barrier 1030 and a mobile phase front 1230 starts to diffuse through the migration zone 1020. Progress of the mobile phase front 1230 along the x-axis of the time sensor strip 1210 indicates elapsed time since the removal of the adhesive layer 1042, which is the application time of the bandage, as described supra.

Example II

Figure 13:
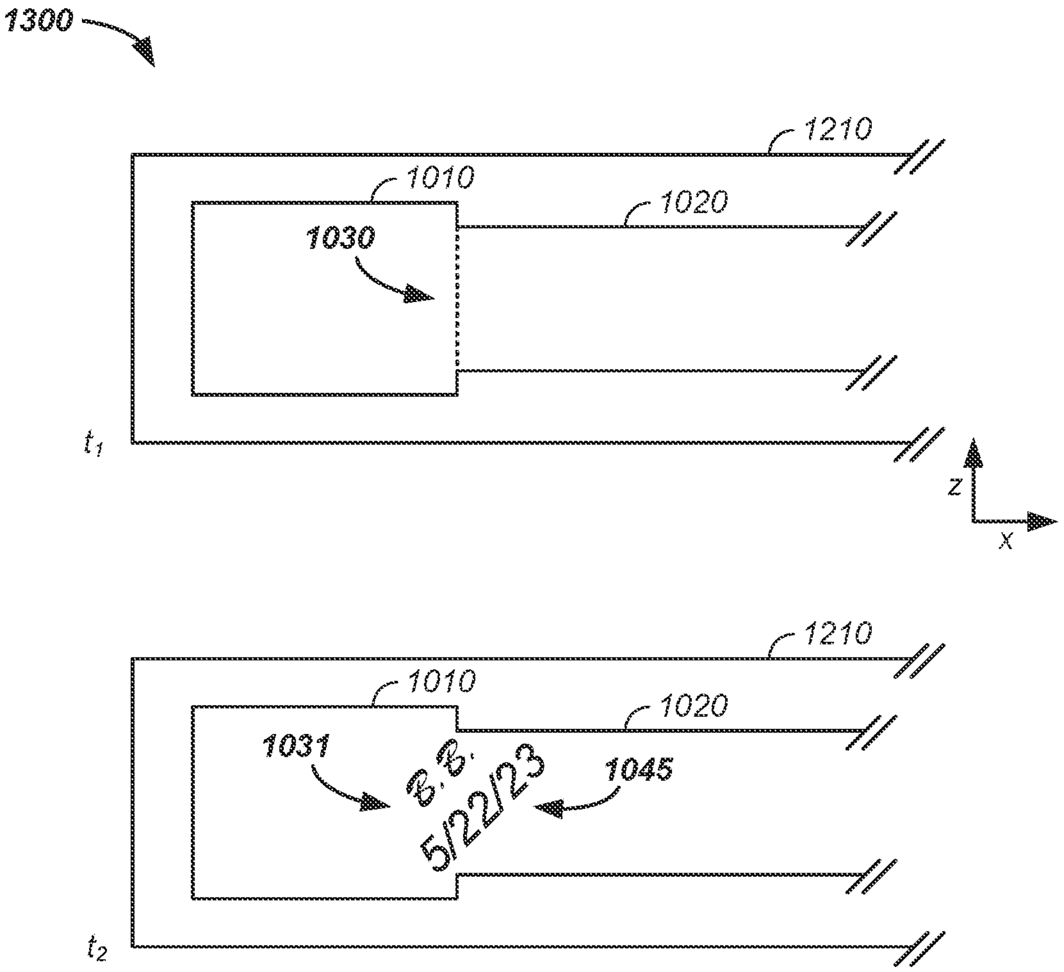
FIG. 13 illustrates a signature activated time sensor.

Referring now to FIG. 13, an example of a signature activated time sensor 1300 is illustrated, which is optionally and preferably an element of the bandage 420 and/or PICC line assembly 900. In this example of a time sensor strip 1210, the time sensor 212 has a reservoir 1010 and a migration zone 1020 on a strip, where the barrier 1030 is a frangible barrier that is ruptured by the downward force of signing and/or dating 1045 over the barrier 1030, such as a frangible seam. The force of signing breaks/ruptures the barrier 1030 resulting in a ruptured barrier 1031, such as at a first time, t1, which initiates movement/diffusion of the mobile phase through the migration zone 1020, as described supra. Again, total movement, not illustrated for clarity of presentation, of the mobile phase front 1230 marks elapsed time since application of the bandage 420 and/or the PICC line assembly 900, when the dated signature was applied.

Example III

Figure 14:
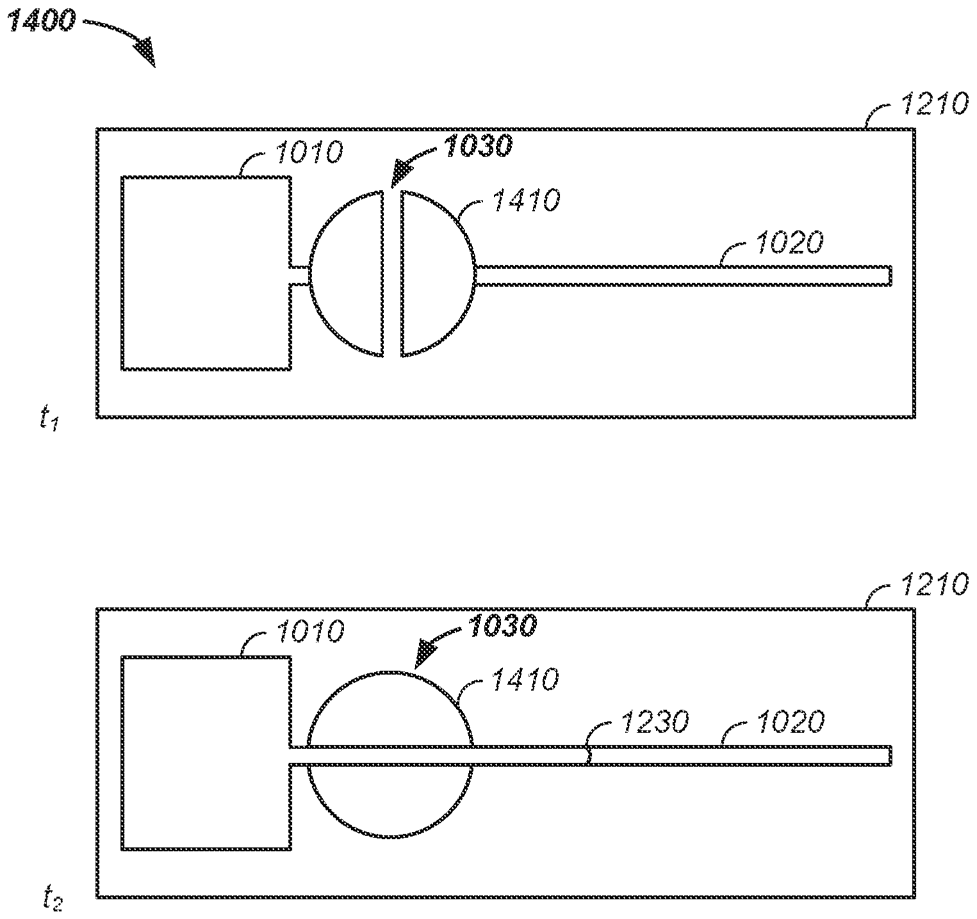
FIG. 14 illustrates a valve activated time sensor.

Referring now to FIG. 14, an example of a valve activated time sensor 1400 is illustrated, which is optionally and preferably an element of the bandage 420 and/or the PICC line assembly 900. In this example of a time sensor strip 1210, the time sensor 212 has a reservoir 1010 and a migration zone 1020 on a strip, where the barrier 1030 is a valve 1410, such as a rotatable valve or a valve opened along an axis. A caregiver opening the valve 1410, such as at a time of application of the bandage 420 and/or PICC line assembly 900, opens the barrier 1030, which starts the migration of the mobile phase. As described supra, total movement of the mobile phase front 1230, through the migration zone 1020, marks elapsed time since application of the bandage 420 and/or the PICC line assembly 900, when the valve 1410 was applied.

Example IV

Figure 15:
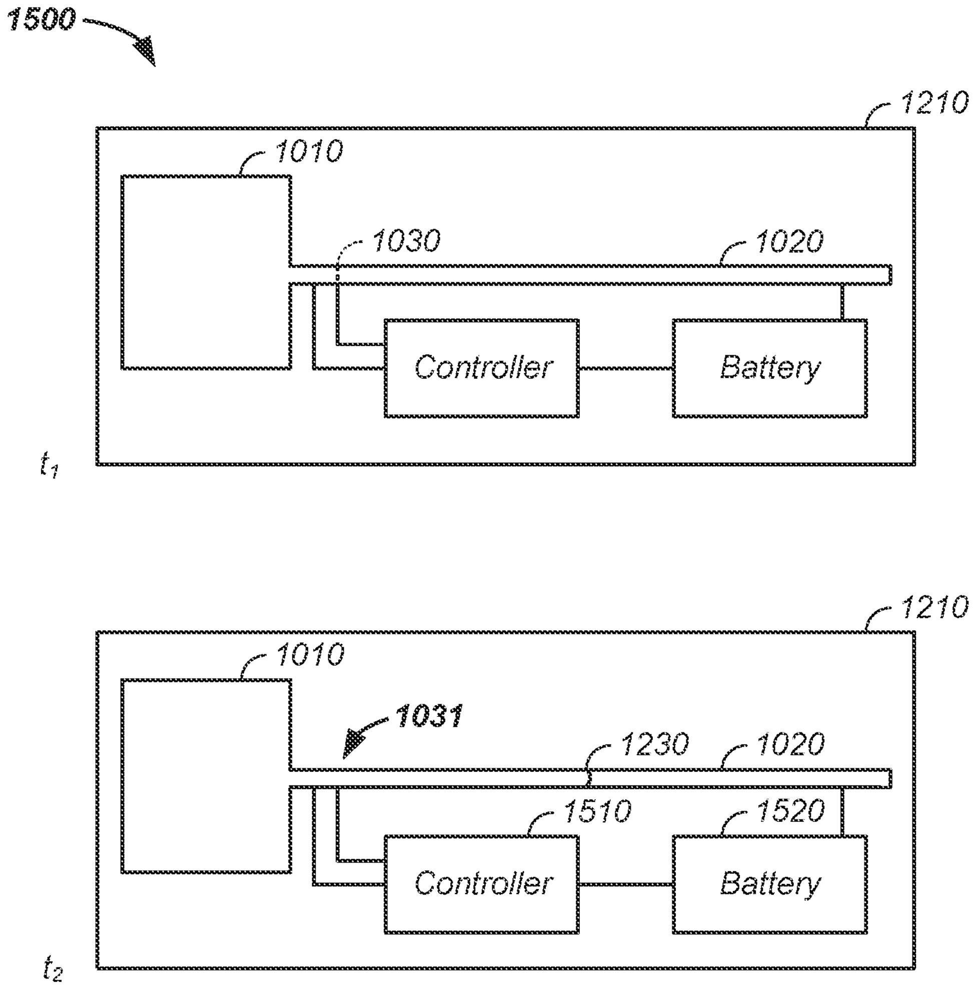
FIG. 15 illustrates a battery powered time sensor.

Referring now to FIG. 15, an example of a battery powered time sensor 1500 is illustrated, which is optionally and preferably an element of the bandage 420 and/or the PICC line assembly 900. In this example of a time sensor strip 1210, the time sensor 212 has a reservoir 1010 and a migration zone 1020 on a strip, where the barrier 1030 is optionally opened through application of a current or voltage and/or through any opening means described herein. In this example, a caregiver simply activates the time sensor, such as through activation of a controller 1510 linked to a battery 1520, such as via depressing a button or throwing a switch, where the controller alters the barrier 1030 into a ruptured barrier 1031. Time passage after opening of the barrier 1030 is marked as described supra. Optionally, the battery provides a potential along the length of the migration zone 1020, which allows movement of the mobile phase via electrophoresis and/or a redox reaction to mark passage of time.

Example V

Figure 16:
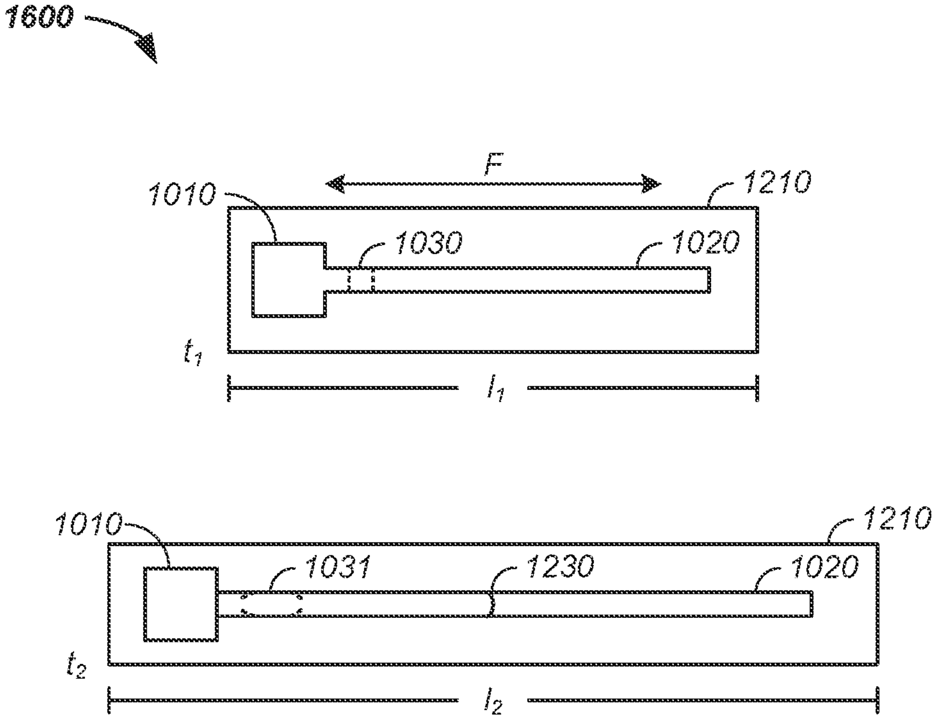
FIG. 16 illustrates a stretch activated time sensor.

Referring now to FIG. 16, an example of a stretch activated time sensor 1600 is illustrated, which is optionally and preferably an element of the bandage 420 and/or PICC line assembly 900, such as attached to the above described adhesive tape 930 aiding secure placement of the PICC line. In this example of a time sensor strip 1210, the time sensor 212 has a reservoir 1010 and a migration zone 1020 on a strip, where the barrier 1030 is optionally opened through a rupturing action resultant from stretching the time sensor strip 1210, bandage 420, and/or adhesive tape 930. As illustrated, the adhesive tape 930 and/or the time sensor strip 1210 is stretched from a first length, $l_1$, to a second length, $l_2$, at the time of application of the bandage 420, adhesive tape 930, and/or PICC line to the patient, where the force used to stretch the bandage 420 and/or adhesive tape 930 ruptures the barrier 1030 resulting in a ruptured barrier 1031. As described supra, rupturing the barrier 1030 initiates movement of the mobile phase in the time sensor where position changes of the mobile phase front 1230 indicates passage of time, such as denoted by the calibration time points 1050 marked on the time sensor, as described supra.

Spine Board

Figure 17A:
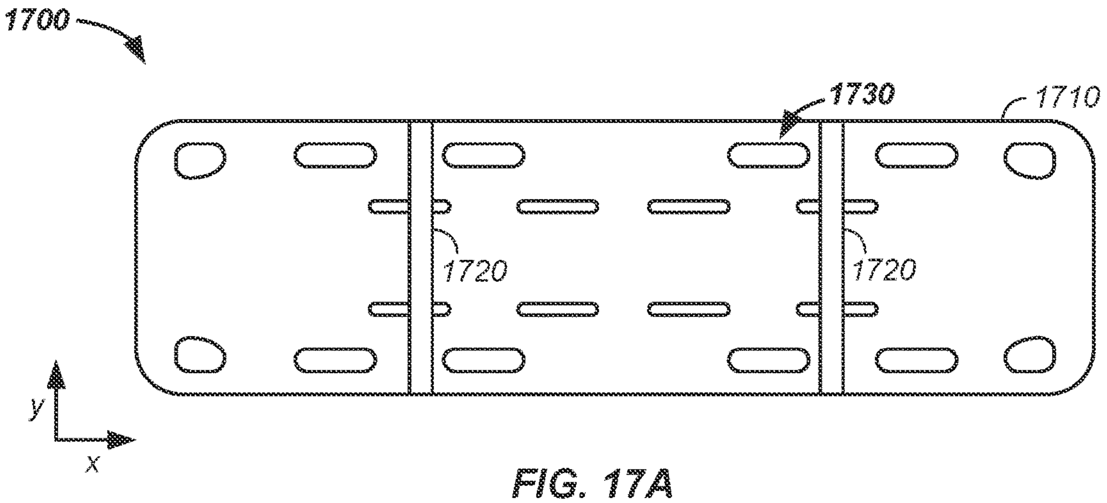
FIG. 17A and FIG. 17B illustrates a padded spine board from a top and side view, respectively.
Figure 17B:
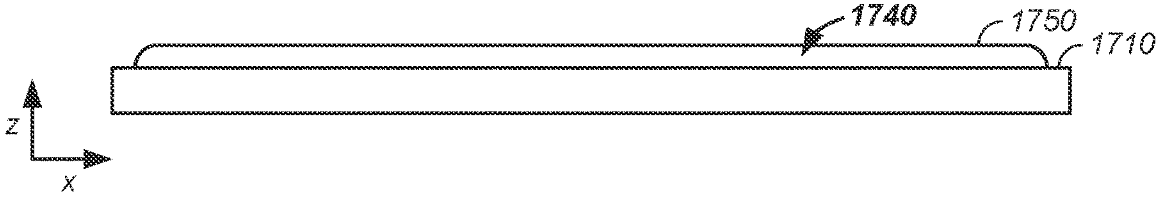

Referring now to FIG. 17A and FIG. 17B, a spine board 1700 is illustrated. The spine board 1700 is illustrated with a rigid back 1710, optional folding axes 1720, and optional openings therethrough 1730, such as for grasping and/or for air circulation. Referring now to FIG. 17B, the rigid back 1710 of the spine board 1700 is illustrated with a foam layer 1740 and/or a viscoelastic foam layer, such as encased in an outer layer 1750 that is approved and readily cleaned, such as an ER cot cover. The foam layer 1740 provides semi-rigid support to the patient that keeps the spine straight and secure, but is softer/more deformable than the rigid back 1710, which gives spinal support while mitigating development of pressure induced wounds, skin breakdown, on the patient.

Still yet another embodiment includes any combination and/or permutation of any of the elements described herein.

Herein, a set of fixed numbers, such as 1, 2, 3, 4, 5, 10, or 20 optionally means at least any number in the set of fixed number and/or less than any number in the set of fixed numbers.

The particular implementations shown and described are illustrative of the invention and its best mode and are not intended to otherwise limit the scope of the present invention in any way. Indeed, for the sake of brevity, conventional manufacturing, connection, preparation, and other functional aspects of the system may not be described in detail. Furthermore, the connecting lines shown in the various figures are intended to represent exemplary functional relationships and/or physical couplings between the various elements. Many alternative or additional functional relationships or physical connections may be present in a practical system.

In the foregoing description, the invention has been described with reference to specific exemplary embodiments; however, it will be appreciated that various modifications and changes may be made without departing from the scope of the present invention as set forth herein. The description and figures are to be regarded in an illustrative manner, rather than a restrictive one and all such modifications are intended to be included within the scope of the present invention. Accordingly, the scope of the invention should be determined by the generic embodiments described herein and their legal equivalents rather than by merely the specific examples described above. For example, the steps recited in any method or process embodiment may be executed in any order and are not limited to the explicit order presented in the specific examples. Additionally, the components and/or elements recited in any apparatus embodiment may be assembled or otherwise operationally configured in a variety of permutations to produce substantially the same result as the present invention and are accordingly not limited to the specific configuration recited in the specific examples.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components.

As used herein, the terms “comprises”, “comprising”, or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus.

Other combinations and/or modifications of the above-described structures, arrangements, applications, proportions, elements, materials or components used in the practice of the present invention, in addition to those not specifically recited, may be varied or otherwise particularly adapted to specific environments, manufacturing specifications, design parameters or other operating requirements without departing from the general principles of the same.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for monitoring a wound site of a patient, comprising the steps of:

applying a bandage to the wound site, said bandage comprising a breakable barrier, said breakable barrier comprising a frangible seam;

signing the bandage with a signature crossing said frangible seam; said step of signing further comprising the step of:

applying a downward signing force across said frangible seam, said downward signing force sufficient to break said frangible seam;

activating a time sensor at an initial time of application of said bandage with said downward signing force; and monitoring elapsed time since application of said bandage through total migration length of a fluid from a reservoir into a migration zone, said reservoir and said migration zone separated by said breakable barrier.

2. The method of claim 1, further comprising the step of:

demarking time through progression of a colored fluid from said reservoir into said migration zone with calibrated time points printed on said bandage.

3. The method of claim 2, further comprising the step of:

securing a PICC line with an adhesive tape.

4. The method of claim 3, further comprising the step of:

monitoring a pH of the wound site with a pH sensor at least partially embedded in said bandage.

5. The method of claim 3, further comprising the step of:

monitoring a temperature of the patient with a temperature sensor at least partially embedded in said bandage.

6. The method of claim 1, further comprising the step of:

rotating a valve to open the barrier.

7. The method of claim 6, further comprising the step of:

demarking time through progression of a colored fluid from said reservoir into said migration zone with calibrated and printed time points on said bandage.

8. The method of claim 7, further comprising the steps of:

monitoring a pH of the wound site with a pH sensor at least partially embedded in said bandage; and monitoring a temperature of the patient with a temperature sensor at least partially embedded in said bandage.

9. The method of claim 1, further comprising the step of:

monitoring pH of the wound site with a pH sensor at least partially embedded in said bandage.

10. The method of claim 1, further comprising the step of:

covering a PICC line with said bandage.

11. The method of claim 1, further comprising the step of:

controlling a movement of a liquid phase from said reservoir into said migration zone through application of at least one of a current and a voltage.

* * * * *